United States Patent
Kanvinde et al.

(10) Patent No.: US 8,730,472 B2
(45) Date of Patent: May 20, 2014

(54) METHOD FOR PREDICTING HAZE IN LUBRICANT BASE STOCKS

(75) Inventors: Atul Gurunath Kanvinde, Mumbai (IN); Charles Lambert Baker, Thornton, PA (US); John T Rizzo, Mantua, NJ (US); Janet Lee Lane, Haddonfield, NJ (US); Roland Bernard Saeger, Runnemede, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 314 days.

(21) Appl. No.: 13/188,979

(22) Filed: Jul. 22, 2011

(65) Prior Publication Data

US 2013/0021607 A1   Jan. 24, 2013

(51) Int. Cl.
*G01N 21/00* (2006.01)

(52) U.S. Cl.
USPC .......................................... 356/337

(58) Field of Classification Search
USPC .......................................... 356/337
See application file for complete search history.

(56) References Cited

U.S. PATENT DOCUMENTS

| 4,728,414 A * | 3/1988 | West et al. | 208/33 |
| 6,468,418 B1 * | 10/2002 | Biscardi et al. | 208/299 |
| 7,875,458 B2 | 1/2011 | Eagan et al. | |
| 2003/0226785 A1 * | 12/2003 | Murphy et al. | 208/18 |
| 2005/0112767 A1 * | 5/2005 | Eagan et al. | 436/55 |
| 2005/0133409 A1 * | 6/2005 | Abernathy et al. | 208/27 |
| 2011/0083994 A1 | 4/2011 | Sirota et al. | |
| 2011/0083995 A1 | 4/2011 | Gleeson et al. | |

FOREIGN PATENT DOCUMENTS

WO   2009064494 A1   5/2009

OTHER PUBLICATIONS

International Search Report and Written Opinion for PCT/US2012/047505 dated Nov. 9, 2012.

* cited by examiner

*Primary Examiner* — Tarifur Chowdhury
*Assistant Examiner* — Omar Nixon
(74) *Attorney, Agent, or Firm* — Robert A. Migliorini; Robinson Clark

(57) ABSTRACT

The invention is a technique for predicting future haze formation in dewaxed, petroleum-derived, lubricant base stocks and, by extension, products made from such base stocks. In general, the technique measures the changes in light scattering caused by the formation and disappearance of wax crystals in a dilute test sample of neat base stock, over the course of a temperature profile. The data obtained is then compared to a previously formulated historical correlation of measurements taken using light scattering data to haze potential. The technique focuses on haze disappearance temperature as a reference point, as opposed to total wax formation. The technique also uses a solvent to accelerate the formation of wax crystals in the test sample. The technique provides a robust early warning system that allows refineries to rapidly and accurately determine the long term haze potential of a base stock production prior to release. The technique can be performed in real time, typically in less than an hour.

22 Claims, 8 Drawing Sheets

PRESENCE OF PARTICLES

METHOD FOR PREDICTING HAZE IN LUBRICANT BASE STOCKS

1.0 BACKGROUND OF THE INVENTION

1.1 Field

The present invention relates to a method for rapidly and accurately predicting the potential for future haze formation in dewaxed, petroleum-derived, lubricant base stocks.

1.2 Description of Related Art

Finished Lubricants Are a Blend Of Base Oil And Various Combinations Of Additive. A typical lubricant comprises at least seventy five percent (75%) by weight base oil and no more than twenty-five percent (25%) by weight additives. Each lubricant is formulated to meet various physical performance specifications such as viscosity, viscosity index, pour point, flash point and density. In addition, each lubricant is formulated to meet specifications relating to its ability to serve as a particular type of engine oil. Specifications vary depending on the identity of the lubricant and, for any given lubricant, are both institute and manufacturer based.

The lubricant base oil, in turn, is formulated from one or more refinery base stocks. Refinery base stocks are manufactured from crude oil distillates (e.g., mineral oil) to meet, and thereafter sold to lubricant manufacturers as meeting, various performance specifications such as viscosity, viscosity index, pour point, cloud point, aromatics content and saturates content. Specifications vary depending on the identity of the base stock and, for any given base stock type, are both institute and manufacturer based.

Refinery base stocks are typically liquid by-products of mineral oils derived form crude oil refining and comprise hundreds, if not thousands, of different hydrocarbons. Typical hydrocarbons in the mineral oils include paraffins, iso-paraffins, naphthenes, aromatics, etc. The mineral oils most suitable for making lubricant base stock tend to have the highest concentrations of paraffins and/or naphthenes.

For a lubricant manufactured using a given base stock or mixture of base stocks to effectively perform its intended function in its intended environment (e.g., internal combustion engines, turbines, hydraulic lines, etc.), it must retain its specification properties and remain liquid even at low temperatures. Toward this end, during the refining process, normal or slightly branched long chain waxes which, due to relatively high melting temperatures tend to solidify easily, are either removed from the mineral oil or converted into non-waxy products. Typical dewaxing processes include: (i) solvent dewaxing where a mixture of waxy mineral oil and solvent is chilled and then filtered or centrifuged to remove wax; and (ii) catalytic dewaxing where the use of a catalyst converts the wax in a mineral oil by cracking/fragmenting it into shorter chain hydrocarbons.

However, no dewaxing process is one hundred percent (100%) effective. Dewaxing processes are designed to remove or convert sufficient wax to meet the requisite base stock property specifications—particularly pour point and cloud point. In other words, the severity of the dewaxing process is linked to the pour point and cloud point required. Thus, a base stock with a relatively high pour point can and will have more residual wax than a base stock with a relatively low pour point. In general, even a properly dewaxed base stock contains as much as one to two percent (1-2%) by weight residual wax.

Further, breakdowns and/or inefficiencies in the dewaxing process can result in higher levels of residual wax in the base stock. The presence of higher than intended quantities of residual wax can be caused by any one of a number of reasons including, but not limited to, the following: (i) leakage of wax through rips or tears in the wax filter cloth used in a solvent dewaxing; (ii) base stock channeling through catalytic beds used in a catalytic dewaxing; (iii) poor catalyst activity or selectivity in catalytic dewaxing due, for example, to catalyst contamination or age; (iv) overloading the dewaxing process (whether solvent or catalytic); and/or (v) using a feed stock different from the composition that a particular site's dewaxing process was designed to optimally process.

The presence of higher than intended amounts of residual wax in a base stock may result in the growth of wax crystals in either the base stock or in products formulated using the base stock. The phase separation of wax crystals from a base stock can occur even under quiescent conditions at ambient temperature. The wax crystals first appear as a visible "haze" of fine particles which ultimately, given sufficient time, accumulate to form larger structures called "flocs." As little as 25-100 ppm phase separated wax can produce haze.

From a customer perspective, the appearance of haze in a base stock has very negative implications on base stock quality. Haze is viewed negatively for a number of reasons. First, wax crystals tend to interfere with the solubility of lubricant additives. Since the properties of a finished lubricant are highly dependent upon additives dispersed in the solution, anything that prevents additives staying in solution is undesirable. Second, wax crystals cause a non-Newtonian increase in low temperature viscometrics in lubricants, which can result in high viscosities and/or poor pumpability at low temperature. Third, wax crystals lessen lubricant filterability since solid or semi-solid wax clogs the pores of the fine filters that are typically used, for example, in combination with circulating lubricant oils such as engine oil. This, in turn, can starve an engine of needed oil. Any of these scenarios can cause a finished lubricant to fail to perform the desired lubricating function. Accordingly, customers associate high quality base stocks with a clear and bright, as opposed to a hazy, appearance. The clear and bright standard is set forth in ASTM D-4176-93 (Reapproved 1997).

Unfortunately, haze may not be visible in a base stock with higher than desired wax content for days, weeks or even months after manufacture. Typically, refineries, in order to minimize storage capacity cost, release each base stock batch within twenty-four (24) hours of production. Therefore, haze issues are often not apparent until the base stock has already left the refinery and, possibly, been incorporated into a base oil and/or lubricant product. Haze may form as the base stock, or products made from the base stock, are stored in customer tanks, warehouses and/or shelves in a quiescent state at ambient or cooler temperatures. Alternatively, haze may form in a finished lubricant as it is utilized by the ultimate purchaser at ambient or cooler temperatures. In each case, the typical result is customer dissatisfaction with the product—which ultimately reflects poorly on the refinery. Accordingly, refineries have a continuing need for faster and more reliable methods of measuring long term haze potential in base stock production prior to release.

Currently, refineries evaluate base stock production using a series of visual and/or viscometric tests. Verifying cloud point, overnight cloud point and confirming a clear and bright appearance (versus hazy appearance) are typical examples of visual tests. Verifying pour point is a typical example of a viscometric test. These visual and viscometric tests are generally sufficient to detect gross deviations from acceptable wax content. Unfortunately, smaller deviations in wax content often have a profound impact on long term haze potential without affecting the outcome of these tests—at least when the tests are conducted close to the time of manufacture. In other words, a base stock prone to long term haze may initially appear clear and bright and may initially meet the requisite pour point and cloud point specifications. In this regard, the current tests are not sufficient. Further, the current tests tend to be very subjective, which causes them to be less reliable.

ExxonMobil Research and Engineering Company previously disclosed a method "for predicting the low temperature viscometric properties of fully formulated lubricating oils based on analyses of the wax content of the basestock used in producing such oils." [See, U.S. Pat. No. 7,875,458 1:2-15.] In that disclosure, "[t]he substitution of an electronic analyzer which measures the onset and degree of haze or wax crystal formation by a change in the transmittance of light or in the degree of intensity of reflected light removes the human element from wax crystal formation determination." [Id. 2:23-27] Unfortunately, even when that technique is used to predict long term haze, instances occur where a base stock passes initial analysis and later exhibits long term haze. While not wanting to be bound by theory, this is likely due to an inability to sufficiently accelerate phase separation of sufficient high melting residual wax, even at cooler temperature, for detection by light scattering in the allotted time.

Refineries need a more robust early warning system to rapidly and accurately predict the potential for long term haze in lubricant base stocks. Further, refineries need assurance that a base stock that appears clear and bright at the time of manufacture will remain so days, weeks or even months later. This need, among others, is met by the present invention.

2.0 BRIEF DESCRIPTION OF THE SEVERAL VIEWS OF THE DRAWINGS

The following drawings are for illustration purposes only.

These drawings are not intended to limit the scope of the present inventions in any way.

3.0 SUMMARY OF THE INVENTION

The invention is a method or technique (as used interchangeably herein) for predicting future haze formation in dewaxed, petroleum-derived, lubricant base stocks and, by extension, products made from such base stocks. In general, the technique measures the changes in light scattering caused by the formation and disappearance of wax crystals in a dilute test sample of neat base stock, over the course of a temperature profile. The data obtained is then compared to a previously formulated historical correlation of light scattering data to haze potential.

According to the method, a test sample is prepared comprising a neat sample of base stock and a solvent that facilitates crystallization of wax components in the base stock. The test sample is then subjected to a temperature profile comprising a sub-ambient cooling step and a subsequent heating step. Changes in light scattering, caused by the formation and disappearance of wax crystals in the test sample, are directly or indirectly monitored over the course of the temperature profile. At least a portion of the light scattering data obtained is then compared to one or more reference points based on historical test data to determine whether the base stock has an acceptable or unacceptable haze potential.

Typically, the method comprises at least four steps. First, a test sample is prepared by taking a neat sample of base stock and, subsequently, diluting the neat sample with a solvent that facilitates crystallization of wax components in the base stock. Second, the test sample is subjected to a temperature ramp. The temperature ramp at least includes a cooling step whereby the test sample is cooled to a sub-ambient target temperature and held there for a period of time sufficient to crystallize high melting wax components in the base stock. The temperature ramp further comprises a subsequent heating step whereby the test sample is heated to a target temperature sufficiently high, and at a rate sufficiently slow, to accurately measure by light scattering the temperature at which the wax crystals fully melts back into solution (i.e., the haze disappearance temperature (HDT). Third, the crystallization and melting of wax crystals in the test sample is monitored during the course of the temperature ramp, by measuring, directly or indirectly, changes in light scattering. The changes in light scattering permit identification of, inter alia, peak crystal formation and HDT. Fourth, and finally, a comparison is made of the HDT determined by light scattering to a HDT reference point. The HDT reference point, which is based on historical data, is the maximum HDT that the base stock should exhibit if it is to remain clear and bright (i.e., haze free) over the course of a typical lubricant manufacture, storage and use lifecycle.

The technique focuses on HDT as a reference point, as opposed to total wax formation, because HDT is a better indicator of the presence or absence of high melting wax. In other words, a base stock with low amounts of residual wax may still exhibit haze if the wax that remains present is predominately of the higher melting variety.

The technique also uses a solvent to accelerate the formation of wax crystals in the test sample. The use of a solvent to enhance haze formation is counter-intuitive, since one would normally expect haze to be more difficult to detect in diluted samples due to lower concentration. However, in this case, the solvent, when combined with the base oil, acts as an antisolvent for the wax component in the base oil and, thereby, drives high melting wax (i.e., the wax most likely to contribute to haze formation) out of the oil faster so that it can be detected more quickly and easily. The solvent may be a single homogeneous solvent or a blend of two or more solvent components. Typically, the solvent or solvent blend has a bulk solubility parameter that is 0.1-2.0 $MPa^{1/2}$ above the solubility parameter of the base oil. Further, if two or more solvent components are employed, then the solvent components typically have a solubility parameter differential no greater than 5 $MPa^{1/2}$. This is most easily achieved by blending two or more commercial solvents. Preferably, the solvent or solvents selected are low molecular weight polar solvents. Typical solvents are ketones. An especially preferred solvent is a blend of methyl iso-butyl ketone (MIBK) and methyl ethyl ketone, (MEK)—said ketones having solubility parameters of 17.2 and 19, respectively.

The method provides a robust early warning system that allows refineries to rapidly and accurately determine the long term haze potential of a base stock production prior to release. Using the technique, refineries are better able to use light scattering techniques, which do not rely on the subjective assessment of the human eye, to ensure the long term stability of base stock appearance and properties. The technique can be performed in real time, typically in less than an hour. As a result, the method increases customer satisfaction in base stock purchased from a refinery and customer confidence in its long term fitness for use in commercial base oils and lubricants. Further, the technique provides sufficiently rapid and reliable results for refineries to make on the fly adjustments (e.g., to dewaxing and other operations) when base stocks with an unacceptable wax content are detected and, thereafter, quickly verify whether the adjustments subsequently made adequately resolve the problem.

These and other features of the invention are set forth in more detail below.

4.0 DETAILED DESCRIPTION OF THE INVENTION

4.1 Definitions

For ease in understanding the invention, the following words and phrases shall have the following meaning:

"Antisolvent," with respect to a designated material (e.g., a wax), means a liquid substance in which the designated material is primarily insoluble (i.e., is more insoluble than soluble) under ambient conditions.

"Base stock" is any refined or synthetic product produced for use in lubricant base oil formulations. Base stocks are generally defined by viscosity grade and produced to a quality to meet an American Petroleum Institute (API) group I, II, III, IV or V quality standard.

"Base oil" is a product, comprising one or more base stocks, produced for use as a virgin oil component, to which various additive packages may be added, to formulate a finished lubricant.

"Lube, "lubricant" and "lubricating oil," as used interchangeably herein, refers a liquid that, when introduced between two moving surfaces, reduces the friction between the surfaces, thereby improving efficiency and/or reducing wear. A lubricant may also function to dissolve or transport foreign particles and distribute heat. Engine/motor oil is an example of a common lubricant.

"Bright stock" means a base stock produced from de-asphalted residual petroleum distillation bottoms.

"Group I," as it applies to base stock, means a petroleum-derived lubricant base stock that is produced to meet API group I quality specifications. API group I specifications include a total sulfur content of greater than 300 ppm, a total saturates content of less than 90 weight percent and a viscosity index (VI) between 80 and 120. Group I base stocks are generally formulated from Neutral or Bright stock by catalytic or solvent dewaxing. Group I base stocks are generally produced to a viscosity grade expressed in Saybolt Seconds Universal (SSU) at 100° F. (e.g., 100, 150, 190, etc. . . . ) and/or to a nominal kinematic viscosity (cSt) measured at a given temperature.

"Group II," as it applies to base stock, means a petroleum-derived lubricant base stock that is produced meet API group II specifications. API group II specifications include a total sulfur content equal to or less than 300 ppm, a total saturates content equal to or more than 90 weight percent and a VI between 80 and 120. Group II base stocks are generally formulated by hydroprocessing followed by catalytic and/or solvent dewaxing. Group II base stocks are generally produced to a viscosity grade expressed in SSU at 100° F. (e.g., 100, 150, 190, etc. . . . and/or to a nominal kinematic viscosity (cSt) measured at a given temperature.

"Group III," as it applies to base stock, means a lubricant base stock that is produced to meeting API group III specifications. API Group III specifications include a total sulfur content of less than 300 ppm, a total saturates content greater than 90 weight percent and a VI of 120 or greater. Group III base stocks are generally formulated from Neutral stock and/or Fischer Tropsch products by catalytic dewaxing. Group III base stocks are generally formulated by hydroprocessing followed by catalytic and/or solvent dewaxing. Group II base stocks are generally produced to a viscosity grade expressed in SSU at 100° F. (e.g., 100, 150, 190, etc. . . . and/or to a nominal kinematic viscosity (cSt) measured at a given temperature.

"Light Neutral," means a Neutral base stock produced to an SSU viscosity grade of less than 250. or typically less than 6 cSt "Heavy Neutral," means a Neutral base stock produced to an SSU viscosity grade of 500 or more. or typically more than 10 cSt "High melting wax" means wax that, due to a relatively high melting point, is prone to form haze under typical lubricant manufacture, storage and use temperatures (e.g., temperatures ranging from ambient to 0° C.). In most cases, high melting wax refers to substantially linear paraffins having a carbon chain length at least greater than 20 and, more typically, greater than 40.

"Medium Neutral" means a Neutral base stock produced to ISO viscosity grade of greater than or equal to 250 and less then 500.

"Neutral" or "solvent Neutral," as used interchangeably herein, as the terms apply to base stocks, mean virgin distillates from a vacuum distillation column.

"Real time" means within eight hours, preferably within two hours, and most preferably within an hour.

"Wax crystals" means solid or semi-solid wax.

All other terms used herein have the meaning commonly understood by those of ordinary skill in the art.

4.2 Light Scattering Equipment

As stated, the technique disclosed herein measures the changes in light scattering caused by the formation and disappearance of wax crystals in a dilute test sample of neat base stock, over the course of a temperature profile. The data obtained is then compared to a previously formulated historical correlation of measurements taken using light scattering data to haze potential. Typically, the light scattering measurements are conducted using a light scattering instrument.

Figure 1A:
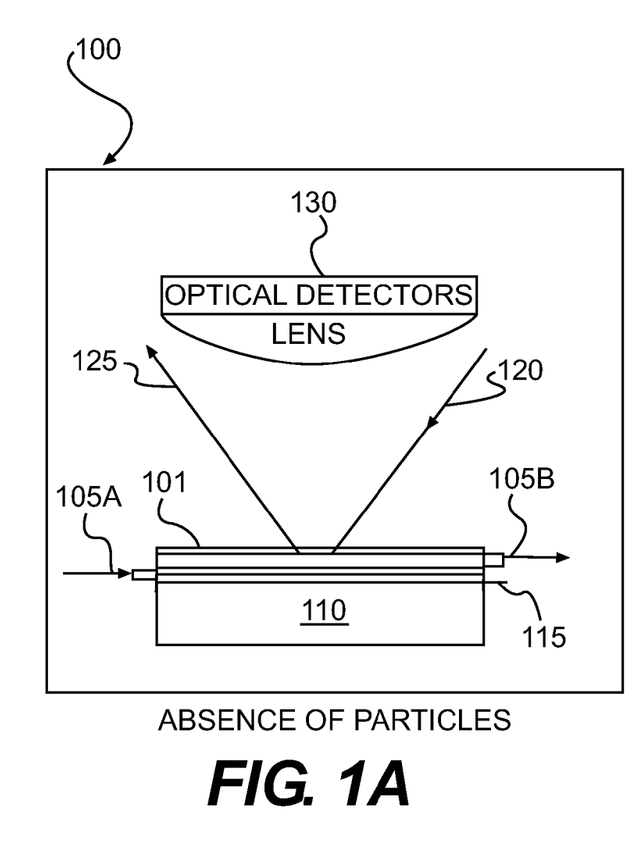
FIGS. 1A and 1B are schematics illustrating the operation of a typical light scattering instrument 100.
Figure 1B:
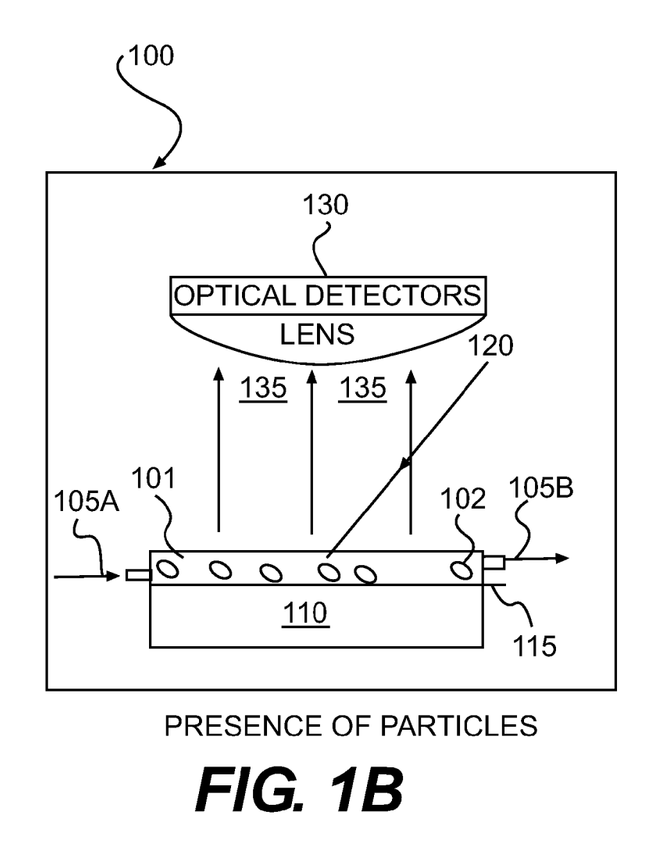

FIGS. 1A and 1B are schematics that illustrate the operation of a typical light scattering instrument 100. The instrument 100 has an inlet 105A for inserting a test sample 101 and an outlet 105B for removing the test sample 101. Although shown in different locations in FIGS. 1A and 1B, the inlet 105A and outlet 105B can be the same site. The cell in which is the test sample is placed, and therefore the sample itself, is typically small. For the purposes of the instrument, test samples can be as small as 0.15 ml.

The instrument 100 has a temperature control device 110 that is run in accordance with instructions supplied by a user programmable computer module (not shown). The computer module governing the temperature control device 110 enables a user to input a temperature profile to which the test sample 101 is to be subjected. In order to reliably execute the temperature profile, the temperature control device 110 receives temperature feedback information from a temperature sensor 115.

The instrument 100 has a source (not shown) of incident light 120 and a light sensor (not shown) for measuring normally reflected light 125. A typical light source is a laser. Absent interference, all of the incident light 120 from the light source should be reflected as normally reflected light 125 along an established trajectory. The instrument 100 also has a light sensor 130 for detecting scattered light 135. Interference will cause some or all of the incident light 120 to be reflected as scattered light 120 in a manner that deviates from the established trajectory. The more interference, the more back-scattering.

The instrument 100 measures light scattering in the test sample 101 as a means of detecting solid wax particulates 102—the presence of which cause interference. If a test sample 101 contains no particulates, then incident light 120 hits test sample 101 and is reflected along an established trajectory. However, if a test sample 101 contains particulates 102 (i.e., wax crystals), then at least some incident light 120 will be scattered and deviates from the established trajectory. The scattered light 120 is detected continuously by light sensor 130. The intensity of the signal for scattered light 135, over time and/or temperature, is then recorded.

An increase in scattering intensity signifies an increase in particulates 102 (e.g., wax crystals) in the test sample 101. Inversely, a fall off in normally reflected light 125 correlates with an increase in the amount of particulates 102. Measuring light scattering directly, or indirectly by measuring changes in normal reflectance, are equivalent techniques embraced by the invention. The latter technique is embraced herein as an "indirect" measure of light scattering.

Various instruments exist, or can be readily fabricated, to practice the present invention. Suitable instruments for making light scattering measurements, directly or indirectly, include the PV70 Analyzer from Phase Technologies (Richmond, British Columbia, Canada) and the Hach 2100AN Turbidimeter (Hach Inc., Colorado). Other instruments suitable for making light transmission measurements, directly or indirectly, are any of the UV-Vis and Near IR spectrophotometers (e.g., Perkin Elmer, Norwalk, Conn.). The PV70 Analyzer made by Phase Technology is a particularly preferred instrument.

Both broad and narrow bands of light within the ultraviolet, visible and/or infrared wavelength region of the spectrum can be measured. However, once a light source and wavelength(s) have been selected, the selection should be held constant thereafter for all base stock test samples of a similar type that are evaluated. Such uniformity insures that the information utilized to generate the historical data base can be used with confidence to evaluate new base stock test samples formulated from recent production runs. Near infrared light, such as that with a wave length ranging from about 700 and about 1000 nm, and preferably ranging from about 820 nm to about 900 nm, is particularly useful as it avoids interference by absorption by some samples, especially those of a dark color.

To better ensure that measurements made with an instrument at one time can be reliably compared to those made at another time, and to better ensure that measurements made on one instrument can be reliably compared to those made on another instrument, the instrument should be calibrated. Light scattering instruments can be calibrated by measuring the signal intensities for standards of known turbidity. Suppliers of such standards include Hach and GFS Chemicals. The instrument signal is correlated to the known values, usually with a linear function. The correlating function is applied to the signal intensity measured on a test sample.

4.2 Neat Sample

At the outset of the method, a sample of neat dewaxed, petroleum derived, base stock from a recent production run is obtained for analysis. The amount of neat sample required is not great. In general, at least about 50 ml of neat base stock is required to accurately do the blending necessary to formulate the test sample. The neat sample can be taken manually or automatically, either in-line during a production run or off-line from a storage tank.

The identity of the dewaxed, petroleum-derived, base stock on which the test technique is employed is not restricted. The technique may be employed with any base stock intended for use in preparing lubricants, including base stock produced by solvent dewaxing, catalytic dewaxing or any other means.

Typically, the base stock is a Neutral base stock (e.g., Light Neutral, Medium Neutral or Heavy Neutral) or a Bright base stock, manufactured to meet group I, group II or group III specifications. Preferably, the base stock is a Neutral or Bright base stock manufactured to meet group I specifications. Of the base stocks that most often exhibit long term haze problems, these base stocks are the most commercially important.

Ideally, the base stock is either a Heavy Neutral or Bright base stock manufactured to meet group I specifications. The intermittent problem of haze is more frequent with higher viscosity grade base stocks. This is probably due to the fact that light grades, such as the Light Neutral, are typically made to lower pour points specifications (e.g., −15° C. pour). Therefore, lighter grades contain relatively low wax content and can tolerate as much as 0.2 weight percent additional residual wax without exhibiting haze or floc. In contrast, heavier grades, such as the Heavy Neutral, are generally made to higher pour point specifications (e.g., −6° C. or −9° C. pour). Therefore, heavier grades contain relatively higher wax content and are much more sensitive to wax contamination. Heavier grades can develop haze or floc with less than 200 ppm additional residual wax.

However, in each case, because the test involves comparisons with correlations based on historical data taken on similar types of base stock, the base stock should be of the same general type for which historical data has been obtained. What defines a base stock of the same general type for use in making comparisons is up to the individual practitioner. The broader the definition, the more generally applicable the test, but less accurate the correlation—which might lead to base stock being rejected that would otherwise pass the test if the test were more tightly tailored. Generally, the comparison will be to a correlation based on historical data from base stocks of the same group (e.g., Group I, II, or III) and class (e.g., Light, Medium or Heavy Neutral or Bright). More preferably, the comparison will be to a correlation that is based on historical data from base stocks of the same group and class produced by a similar method (e.g., solvent dewaxing or catalytic dewaxing). Ideally, the comparison will be to a correlation that is based on historical data from base stocks of the same group and class produced by a similar method at a given site.

Optionally, if extraneous material (other than wax crystals) is present in the neat sample, then the neat sample can be filtered with a relatively course filter. This step is not generally required. When this step is performed, the filter employed should not be so fine that it removes wax particulates. Accordingly, for this optional step, a filter having a pour size of at least about 1 micron is typically utilized.

4.4 Test Sample Comprising Neat Sample and Solvent

The test method employs a test sample preparation step wherein a neat sample of base stock is diluted with solvent. The solvent accelerates crystallization of haze-forming wax components, thereby making the rapid detection of haze-forming wax components by light scattering more accurate and reliable.

The use of a solvent to enhance haze formation is a counter-intuitive, since one would normally expect haze to be more difficult to detect in diluted samples due to lower concentration. However, in this case, the solvent, when combined with the base oil, acts as an antisolvent for the wax components in the base oil and, thereby, drives high melting wax (i.e., the wax most likely to contribute to haze formation) out of the oil faster so that it can be detected more quickly and easily. In other words, the solvent adjusts the solubility of the entire mixture in a manner that increases the difference between the solubility parameter of entire mixture and the specific solubility parameter of the wax components therein.

The identity of the solvent is not limited as long as it is miscible with the base stock at ambient temperature and pressure and facilitates the crystallization of wax components. The identity of the optimum solvent will also vary a bit depending on the composition (i.e., type) of base stock being tested. The solvent may be a single homogeneous solvent. Alternatively, the solvent may be a composition comprising two or more different types of solvents. Suitable solvents can be determined empirically.

Particularly effective solvent or solvent blends typically have a bulk solubility parameter that is at least $0.1$ $MPa^{1/2}$ above the base oil in order to make a large enough solubility change in the base oil/wax blend to facilitate high melting wax separating from solution during the test period. Most base oils have a solubility parameter ranging from 17.0 to 17.5 $MPa^{1/2}$—as compared to wax which has a fairly consistent solubility parameter of about 16.9 $MPa^{1/2}$. This effectively means that the solvent should have a solubility parameter at least 17.1 $MPa^{1/2}$ and, for more universal base oil applicability, a solubility parameter of at least 17.6 $MPa^{1/2}$. In addition, effective solvent or solvent blends do not have a bulk solubility parameter that is so high that all the wax (including relatively lower melting wax) comes out of solution during the test period. Typically, this means using a solvent or solvent blend having a solubility parameter that is 0.1-2.0 $MPa^{1/2}$, more preferably 0.2-2.0 $MPa^{1/2}$, even more preferably 0.3-1.5 $MPa^{1/2}$, and ideally 0.5-1.0 $MPa^{1/2}$ above the solubility parameter of the base oil. In addition, in solvent blends, the delta between the highest and lowest solubility parameters of the solvent components (i.e., the "solubility parameter differential") is typically no greater than 5 $MPa^{1/2}$, preferably no greater than 4.5 $MPa^{1/2}$ and ideally no greater than 4 $MPa^{1/2}$. Compilations of solubility parameters for various compounds are well known in the art. One suitable tabulation can be found in the Polymer Handbook, 4th edition, Brandrup, J., Immergut, Edmund H., Grlke, Eric A., Abe, Akihiro, Bloch, Diniel R., John Wiley & Sons (2005).

Preferred solvents are low molecular weight compounds, preferably compounds that have a molecular weight below 300, more preferably below 200 and most preferably below 150. A low molecular weight solvent is preferred because it helps magnify the solubility differences between the wax and the oil. While not wishing to be bound by theory, this is likely due to the fact that like dissolves like and, therefore, low molecular weight solvents are more likely to exert an antisolvent effect on the high molecular weight wax components in the base oil.

Preferred solvents are also polar molecules (e.g., a solvent containing oxygen and/or nitrogen functionality). A polar solvent is preferred because it helps magnify the solubility differences between the wax and the oil. While not wishing to be bound by theory, this is likely due to the fact that like dissolves like and, therefore, polar solvents are more likely to exert an antisolvent effect on the non-polar wax components in the base oil.

Suitable solvents generally include a blend of low molecular weight compounds such as ketones, toluene, ethers (e.g., di-methyl ether and trimethyl ether) and acetone. Ketone blends, such as a blend of MEK and MIBK, are particularly useful.

A blend of ketones, such as MEK and methyl isobutyl ketone (MIBK), is particularly effective as the solvent. MEK tends to encourage wax to precipitate. MIBK tends to dissolve wax. The delta in the solubility parameters of MEK and MIBK is 1.8 $MPa^{1/2}$ (i.e., 19 $MPa^{1/2}$ for MEK versus 17.2 $MPa^{1/2}$ for MIBK). Other suitable solvent blends include MEK/toluene and MEK/heptane. The delta in the solubility parameters of MEK and toluene is 0.8 $MPa^{1/2}$ (i.e., 19 $MPa^{1/2}$ for MEK versus 18.2 $MPa^{1/2}$ for toluene) and for MEK is 3.9 $MPa^{1/2}$ (i.e., 19.0 $MPa^{1/2}$ for MEK versus 15.1 $MPa^{1/2}$ for heptane).

Ideally, the solvent is a blend of MEK and MIBK in a respective weight ratio of 10-90:90-10, preferably 20-80:80-20 and more preferably 25-75:75-25. For Heavy Neutral, a blend of MEK and MIBK in a respective weight ratio 20-80:80-10, more preferably 30-70:70-30, and most preferably approximately 50:50 is particularly effective. For Bright base stock, a blend of MEK and MIBK in a respective weight ratio of 10-50:90-50, more preferably 20-40:80-60, and most preferably approximately 30:70, is particularly effective.

The ratio of base stock to solvent utilized in the method will vary a bit depending on the base stock type and the solvent selected. Therefore, this ratio is not limited as long as the solvent is at least half the weight of the mixture. Preferably, the weight ratio of base stock to solvent is 1:1-5, more preferably, 1:1-4.5 and even more preferably 1:1-3.5. For example, for Heavy Neutral, the weight ratio of base stock to a solvent blend of MEK and MIBK is typically 1:2-4, preferably 1:3-4 and most preferably approximately 1:3.2. In further example, for Bright base stock, the weight ratio of the base stock to a solvent blend of MEK and MIBK is typically 1:1-3, preferably 1:1.5-2.5 and most preferably approximately 1:2.

For each base stock type, once the solvent is selected, it should be used consistently thereafter to insure good comparative results. Similarly, for each base stock type, once a ratio of base stock to solvent is selected, it should be used consistently thereafter to insure good comparative results.

4.5 Temperature Profile

The testing method of the current invention employs a temperature profile. The temperature profile at least comprises a cooling step where the test sample is cooled to a specific target temperature, followed by a soak at that target temperature to precipitate out wax crystals, followed by a warm up step to re-dissolve the wax in the solvent phase. Optionally, the temperature profile may also comprise an initial pre-heating step.

a. Preheating

It is good laboratory practice (but not required) to pre-heat the test sample above ambient temperature prior to testing. Generally, the pre-heating step is conducted in the testing device to a target temperature sufficient to melt any wax crystals that theoretically might already exist in the test sample. This pre-heating step insures that light scattering measurements taken at the outset of the test method represent an accurate baseline. In other words, this pre-heating step insures that light scattering measurements taken immediately prior to the cooling step represent the test sample without any wax crystals. Generally, this pre-heating step is conducted to a target temperature ranging from 40° C. to 60° C. Generally, the sample is held at the target temperature for a time period ranging from 100 to 800 seconds.

The specific rate at which the temperature is increased during the pre-heating step is not important. Nor is it important that the pre-heating step be performed consistently from test sample to test sample. As stated, this is an optional step. Absent a major production problem, base stock tested soon after production should have little, if any, wax crystal content at ambient temperature and pressure. The pre-heating step, however, insures this is the case. The preheating step can be conducted in a single step using a consistent heating ramp to a final target temperature or step wise using multiple heating ramps and/or intermediate target temperatures on the way to a final target temperature.

b. Cooling

The temperature profile comprises at least one cooling step. In the cooling step, the temperature is dropped to a target temperature that is below ambient temperature and held at the target temperature for a period of time. The final determination of what constitutes the optimum target temperature and holding time in the cooling step will vary a bit depending on the base stock type and solvent selected. Therefore, this decision is ultimately left to the discretion of the practitioner. However, the target temperature should be low enough, and the holding time at the target temperature long enough, that most, if not all, of the high melting wax that tends to generate haze crystallizes. This is what enables a meaningful comparison to be drawn between the light scattering data taken and the propensity of the base stock to exhibit long term haze based on a historical correlation. Inversely, the target temperature needs to be high enough that the wax crystals formed are not so voluminous that the resulting light scattering intensity overwhelms the measurement capacity of the analyzer. For example, the PV70 Analyzer from Phase Technologies typically only measures light scattering intensity up to 200 intensity units. Further, the holding time at a given target temperature should be long enough to achieve a peak in the rate of change in light scattering intensity, indicating that the majority of the wax that will phase separate into crystals at the selected target temperature has already phase separated. Basically, the holding time is maintained until the measure of total crystal content by light scattering approaches levels off to an approximate steady state, with only a small amount of additional crystal formation over time.

Preferably, the test sample is cooled to, and then held at, a target temperature that is below 0° C. and above the base stock's cloud point. Preferably, the holding time at the cooler target temperature ranges from 1 to 120 minutes, preferably 5 to 60 minutes, and more preferably 5 to 30 minutes. The cooling step is the longest step in the process. Therefore, selecting a temperature that minimizes the cooling period without significantly impacting the reliability of the test results minimizes turn around time and, thereby, increases the usefulness of the process. For each base stock type, once a target temperature and holding time is selected, it should be used consistently thereafter (at least for test samples of similar type) to insure good comparative results.

The specific rate at which the temperature drops to the target temperature during the cooling step is not particularly important. Using a slower or faster cooling ramp to the final target temperature merely reduces or increases, respectively, the holding time necessary at the target temperature to achieve the desired result—namely, a test sample wherein the haze forming wax has crystallized. Typically, the sample is cooled at a rate ranging from 0.5 to 20° C. per minute and, more preferably, 5 to 15° C. per minute. The temperature drop can be conducted in a single step using a consistent cooling ramp to a final target temperature, or step wise using multiple cooling ramps and/or intermediate target temperatures on the way to a final target temperature. However, a steady controlled descent is preferred. For each base stock type, once the cooling ramp is selected, it should be used consistently thereafter to insure good comparative results.

c. Heating

The temperature profile further comprises at least one heating step that is conducted after the cooling step. The heating step initiates melting, or re-dissolving, of the crystallized wax. Preferably, the test sample is heated to a target temperature sufficiently high enough, and at a rate that is sufficiently slow enough, to accurately measure by light scattering the temperature at which all of the crystallized wax formed during the cooling step has fully melted back into solution (i.e., the HDT). In other words, the test sample is heated to a target temperature sufficiently high enough that the light scattering measurements observed return to the baseline. Generally, a target temperature of at least 0° C., preferably at least 5° C. and more preferably at least 10° C. is sufficient for this purpose.

The temperature increase can be conducted in a single step using a consistent heating ramp to a final target temperature, or step wise using multiple heating ramps and/or intermediate target temperatures on the way to a final target temperature. However, a step wise increase is preferred.

For example, the test sample can be heated to a first target temperature that ranges from −10° C. and 10° C., preferably from −5° C. and 5° C., and ideally is about 0° C.—at a rate ranging from 0.1 to 10° C. per minute, preferably from 0.1 to 5° C. per minute, and ideally ranging from 1 to 3° C. per minute. This first target temperature is the temperature at which base stock that is unlikely to exhibit haze should exhibit an HDT based on historical data. At the first target temperature, a short temperature hold is generally performed, ranging anywhere from a few seconds to five minutes. The temperature hold insures that any failure to observe an HDT measurement at or below the first target temperature point is not due to the speed of the ramp. Thereafter, the temperature is increased again, generally at the same rate, to a second target temperature that is generally high enough to generate an HDT in samples of the given base stock type if one has not already been observed. Typically, the second target temperature is 5 to 20° C. higher than the first target temperature.

For each base stock type, once the heating ramp is selected, it should be used consistently thereafter to insure good comparative results. After this heating step is complete, the test sample is generally allowed to return to ambient temperature. Thereafter, it can be either discarded or stored for further observation and development of historical data, whichever is desired.

4.6 Light Scattering Measurements

Changes in diffusive light scattering from the test sample are monitored directly and/or indirectly over the course of the temperature profile. These changes correlate to the formation and disappearance of wax crystals in the test sample. The monitoring may be done continuously or periodically. Typically, sufficient light scattering data points are taken to accurately represent (a) the baseline, (b) the change in wax crystal formation during the cooling step; and (c) the HDT. Typically, light scattering data points are taken at least about every one (1) second throughout the process.

The light scattering measurements taken at the start of the test, at ambient temperature (~20° C.) or after the pre-heating step (if utilized), define the baseline scatter. As the sample is cooled, the wax starts to precipitate out leading to an increase in the light scattering. The peak light scattering represents the maximum amount of wax that precipitates at the test temperature. This peak has been found to have a correlation with the wax content by DSC.

During the warm up cycle, the precipitated wax gradually re-dissolves in the solution and shows a gradual drop in the light scattering intensity. The slope of the curve is an indication of how the crystallized wax re-dissolves in the solvent mixture. The temperature at which the light scattering returns to baseline is defined as the HDT for that base stock test sample. The HDT is close to the thermodynamic dissolution temperature above which all existing haze in the sample will dissolve and, therefore, where haze can never form.

4.7 Comparison with Historical Information

The light scattering data obtained is then compared to a correlation based on historical data generated from previous light scattering measurements taken on base stocks of a similar type treated in a similar manner (e.g., same solvent, base stock to solvent ratio and temperature ramp). The correlation is a correlation is made by observing light scattering data obtained from historical samples that did and did not exhibit long term haze. Obviously, the most reliable and robust correlations are obtained by representing the widest range of residual wax types and concentrations in the data pool used to make the correlation for a defined type of base stock.

In order to ensure the reproducibility and reliability of the data, it is important to be as consistent as possible with respect to those parameters, measurements and steps which are subject to variability. For example, when a solvent, base stock to solvent ratio and temperature profile are chosen, it is important to use similar, and preferably identical, constraints with respect to all base stock samples used to create the data base and all base stock unknowns subsequently evaluated. This removes sources of unanticipated variance. The dimensions of the test cells, the material used for test cell fabrication, the light source, the wavelengths measured, the measurement device, etc. . . . , should also be kept as uniform and consistent as possible between samples to eliminate any variable other than residual wax contamination.

The historical data can be generated from test samples prepared from prior production runs of a similar type base stock (e.g., base stock of the same group meeting a certain target pour point and cloud point). Alternatively, the historical data may also be generated, either in whole or in part, from test samples prepared from a similar type base stock having a known quantity of wax that is, thereafter, spiked with varying amounts of additional wax.

Preferably, the HDT data obtained for a base stock test sample is compared to a historical correlation between HDT and long term haze. Accordingly, if the HDT of a test sample exceeds an acceptable HDT value, then the base stock from which the test sample was taken fails (i.e., is deemed to possess an unacceptable potential for long term haze). Inversely, if the HDT of the test sample is at or below the acceptable HDT value, then the base stock from which the test sample was prepared passes (i.e., is deemed unlikely to exhibit long term haze).

The HDT is deemed the best reference point for determining long term haze potential in base stock because it is indicative of the point where all wax particles, including the high melting wax particles that have the highest impact on long term haze, melt. Above this temperature, a base stock cannot develop haze. Accordingly, a sufficiently low HDT demonstrates good low temperature properties with respect to stability against long term haze. While not wishing to be bound by theory, it is believed that the sheer amount of wax particles obtained during the cooling step is not as critical to determining haze potential as is the distribution of high versus low melting wax particles. In other words, a test sample might contain relatively few wax particles after the cooling step, but if a large percentage of those wax particles are high melting wax particles, then long term haze may still ensue.

Obviously, the deeper the historical database used to determine the HDT reference point, the more reliable the reference point. For Heavy Neutral and Bright base stock, it has been determined that a test sample with a HDT of less than or equal to 0° C. is a good indicator that the base stock will not develop long term haze and a test sample with a HDT greater than 0° C. is a good indicator that the base stock is likely to form long term haze. Typically, a test sample with an HDT greater than 0° C. is indicative of a base stock that is likely to form haze and, therefore, unsuitable for release.

4.8 Other Embodiments

Different aspects of the invention can be mixed and matched. Accordingly, there are many alternative embodiments to the invention.

In a particularly detailed embodiment, the invention is a real time method for predicting future haze formation in a group I base stock selected from Heavy Neutrals and Bright base stock. In this embodiment, the invention comprises at least four steps. The first step is diluting a sample of the base stock in a solvent comprising a 10:90-90:10 blend of MEK and MIBK, at a base stock to solvent ratio weight range of 1:1-5. The second step is subjecting the test sample to a temperature ramp that comprises at least the following segments in the following order: (a) a pre-heating step, where the test sample is first heated for a time and to a temperature sufficient to melt crystallized wax already present in the test sample in order to obtain a more reliable light scattering measurement to serve as a baseline; (b) a cooling step whereby the test sample is cooled to, and held at, a target temperature that is below 0° C. and above the base stock's cloud point, for a period ranging from 5 to 60 minutes, in order to crystallize high melting wax components in the base stock, and (c) a second heating step whereby the test sample heated at a rate ranging from 0.1 to 1° C. per minute to temperature that is at least above 0° C., in order to measure the temperature at which the crystallized wax has fully melted back into solution (i.e., the HDT). The third step is monitoring the crystallization and melting of wax, during the course of the cooling and heating temperature ramp, by measuring changes in light scattering that correspond to the formation and melting of wax crystals in the test sample. The fourth step is utilizing a HDT as an indicator of long term haze potential, wherein a HDT greater than 0° C. is an indicator that the base stock has an unacceptable risk of forming long term haze.

In this more particular embodiment, when the base stock is a Heavy Neutral, the MEK to MIBK weight ratio ranges from 20-80:80-20 and is preferably 50:50. Further, the weight ratio of base stock to solvent ranges from 1:2-4 and is preferably approximately 1:3.2.

In this more particular embodiment, when the base stock is Bright, the MEK to MIBK weight ratio ranges from 20-40 to 80:60 and is preferably 30:70. Further, the weight ratio of base stock to solvent ranges from 1:1-3 and is preferably approximately 1:2.

4.9 Benefits

The method provides a robust early warning system that allows refineries to rapidly and accurately determine the long term haze potential of a base stock production prior to release. Using the technique, refineries are better able to use light scattering, which does not rely on the subjective assessment of the human eye, to ensure the long term stability of base stock appearance and properties. The technique can be performed in real time, typically in less than an hour. As a result, the method increases customer satisfaction in base stock purchased from a refinery and customer confidence in its long term fitness for use in commercial base oils and lubricants. Further, the technique provides sufficiently rapid and reliable results for refineries to make on the fly adjustments (e.g., to dewaxing and other operations) when base stocks with unacceptable wax content or composition are detected and, thereafter, quickly verify whether adjustments subsequently made adequately resolve the problem.

4.10 Examples

The following examples describe the invention in more detail as it pertains to group I Heavy Neutral and Bright base stock.

a. Example 1

A neat sample of a Heavy Neutral, 600N, was taken from a storage tank and diluted with a solvent composition. The solvent composition used was a 50:50 weight ratio MEK: MIBK mixture. The weight ratio of oil: solvent was 1:3.2. Light scattering measurements were then taken over a temperature profile on a 70 Series Laboratory Analyzer made by Phase Technology, 11168 Hammersmith Gate, Richmond, BC Canada V7A 5H8.

Figure 2:
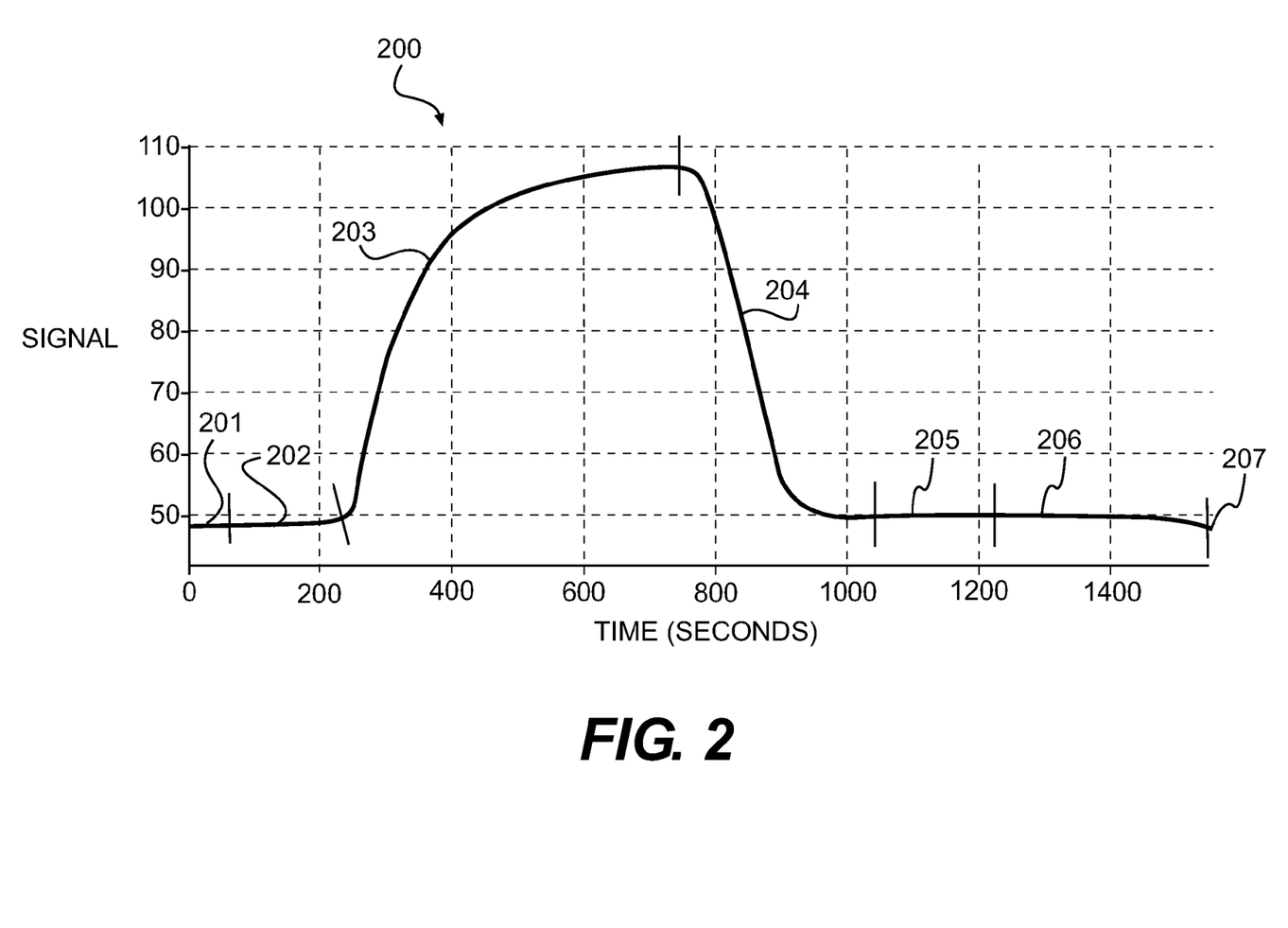
FIG. 2 is a plot 200 showing light scattering intensity (or signal strength) versus time, over the course of a temperature profile, for a sample of a Heavy Neutral "Americas CORE" brand base stock with a viscosity of 600 Sabolt Universal Seconds (AC 600N) that was deemed acceptable using the testing technique of the invention.

FIG. 2 provides a plot 200 of light scattering intensity (or signal strength) versus time over the temperature profile for the Heavy Neutral, 600N. The plot 200 can be split into several sections corresponding to separate portions of the temperature ramp. Section 201 represents a temperature hold, or soak, at 20° C. starting a 0 seconds and ending at 60 seconds. This is the portion of the temperature ramp where the baseline is taken. Section 202 represents a cooling ramp to −10° C. at 10° C./minute, starting at 60 seconds and ending at 240 seconds. This initiates wax crystallization. Section 203 represents a temperature hold, or soak, at −10° C., starting at 240 seconds and ending at 740 seconds. This forces the wax out of the solvent mixture and results in a gradual increase in signal intensity. Section 204 represents a warming ramp to 0° C. at 2° C./minute, starting at 740 seconds and ending at 1040 seconds. This initiates melting, or re-dissolving, of the crystallized wax. The slope of the curve is an indication of how the crystallized wax re-dissolves in the solvent mixture. Section 205 represents a temperature hold, or soak, at 0° C. for 180 seconds, starting at 1040 seconds and ending at 1220 seconds. Before the end of this soak period, all the crystallized wax should be back in the solvent mixture and the signal back to the baseline intensity. Section 206 represents a temperature warming ramp to 10° C. at 2° C./minute, starting at 1220 seconds and ending at 1520 seconds. This warm up assists in dissolving any residual wax back into the solvent mixture. Section 207 represents a temperature hold, or soak, at 10° C. for 10 seconds, starting at 1520 seconds and ending at 1530 seconds.

Note that the signal strength in section 205, during the 0° C. soak period, is very low, relatively unchanging, and compares nicely to the baseline signal strength in section 201. Based on historical data for Heavy Neutral, this is indicative of a base stock that will not form long term haze. If this were not the case, and the signal strength in section 205 were noticeably higher compared to the baseline, and still changing, then the batch of base stock would be rejected as being likely to form long term haze. In this manner, the technique is able to differentiate between clear and bright and potentially haze samples.

FIGS. 3, 4, 5 and 6 illustrate that the new test method is sensitive to detect changes in the residual wax content of the oil. Four neat samples of Heavy Neutral, 600N were taken from a storage tank and diluted with a solvent composition. However, in this case, three samples were doped with 0.1%, 0.2% and 0.5% by weight slack wax, respectively. The oil with 0.5% by weight wax was cloudy at room temperature. The oil with 0.1% and 0.2% by weight wax appeared clear and bright.

The solvent composition used was a 50:50 weight ratio MEK: MIBK mixture. The weight ratio of oil: solvent used was 1:3.2. Light scattering measurements were then taken over the same temperature profile on a 70 Series Laboratory Analyzer made by Phase Technology, 11168 Hammersmith Gate, Richmond, BC Canada V7A 5H8.

Figure 3:
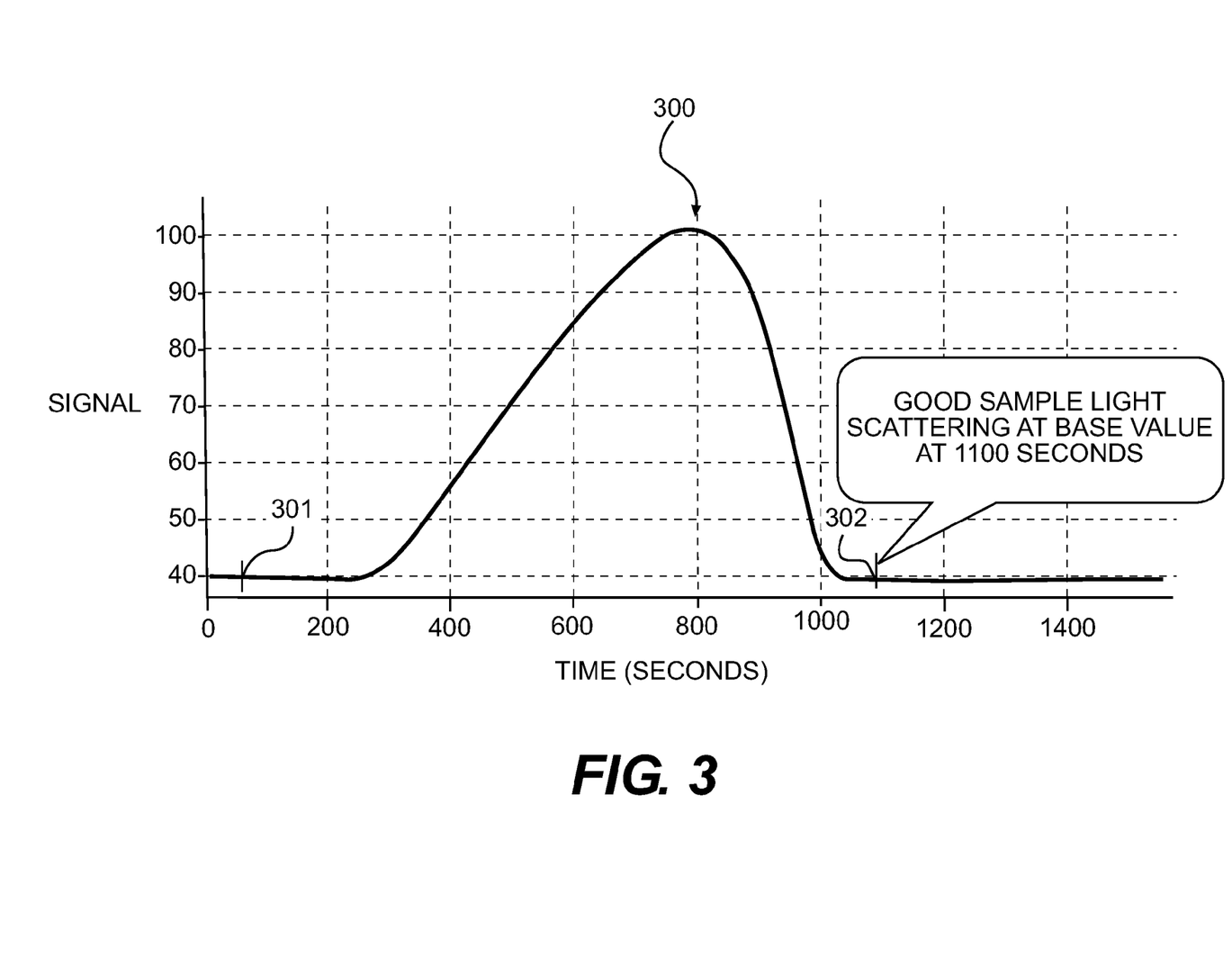
FIG. 3 is a plot 300 showing light scattering intensity versus time, over the course of a temperature profile, for another sample of AC 600N that was deemed acceptable using the technique of the invention.

FIG. 3 shows the light scattering signal strength versus time curve 300 for the sample doped with no wax. The signal strength at point 302, which is approximately 1100 seconds into the process during the 0° C. hold period, is almost identical to the baseline measurement 301 taken at the outset of the process. Further, the slope of changes in the baseline is flat. This test sample would pass. The low signal and flat slope during the period the test sample is being held at 0° C. means that the HDT of the test sample is below 0° C. and the base stock represented by the test sample is unlikely to form long term haze.

Figure 4:
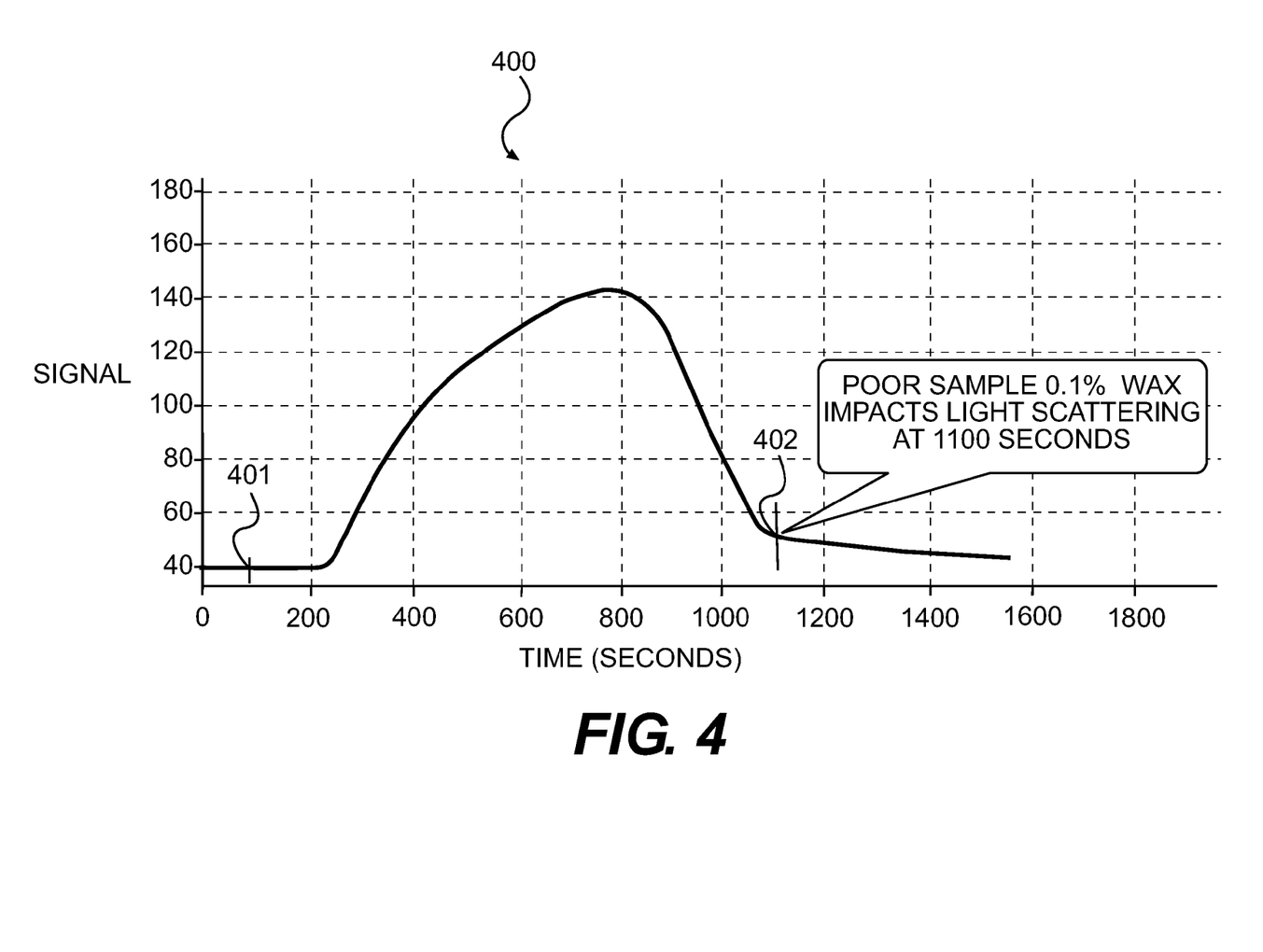
FIG. 4 is a plot 400 illustrating how the plot 300 in FIG. 3 changes when the sample of AC 600N in FIG. 3 is doped with 0.1% by weight wax and is no longer acceptable.

FIG. 4 shows the light scattering signal strength versus time curve 400 for an identical sample doped with 0.1% by weight wax. The signal strength at point 402, which is approximately 1100 seconds into the process during the 0° C. hold period, is noticeably higher than in FIG. 3 and, more importantly, noticeably higher than the baseline measurement 401 taken at the outset of the process and still changing. This test sample would not pass. The higher signal and noticeably steeper curve slope during the period the test sample is being held at 0° C. means that the HDT of the test sample is above 0° C. and the base stock represented by the test sample is likely to form long term haze.

Figure 5:
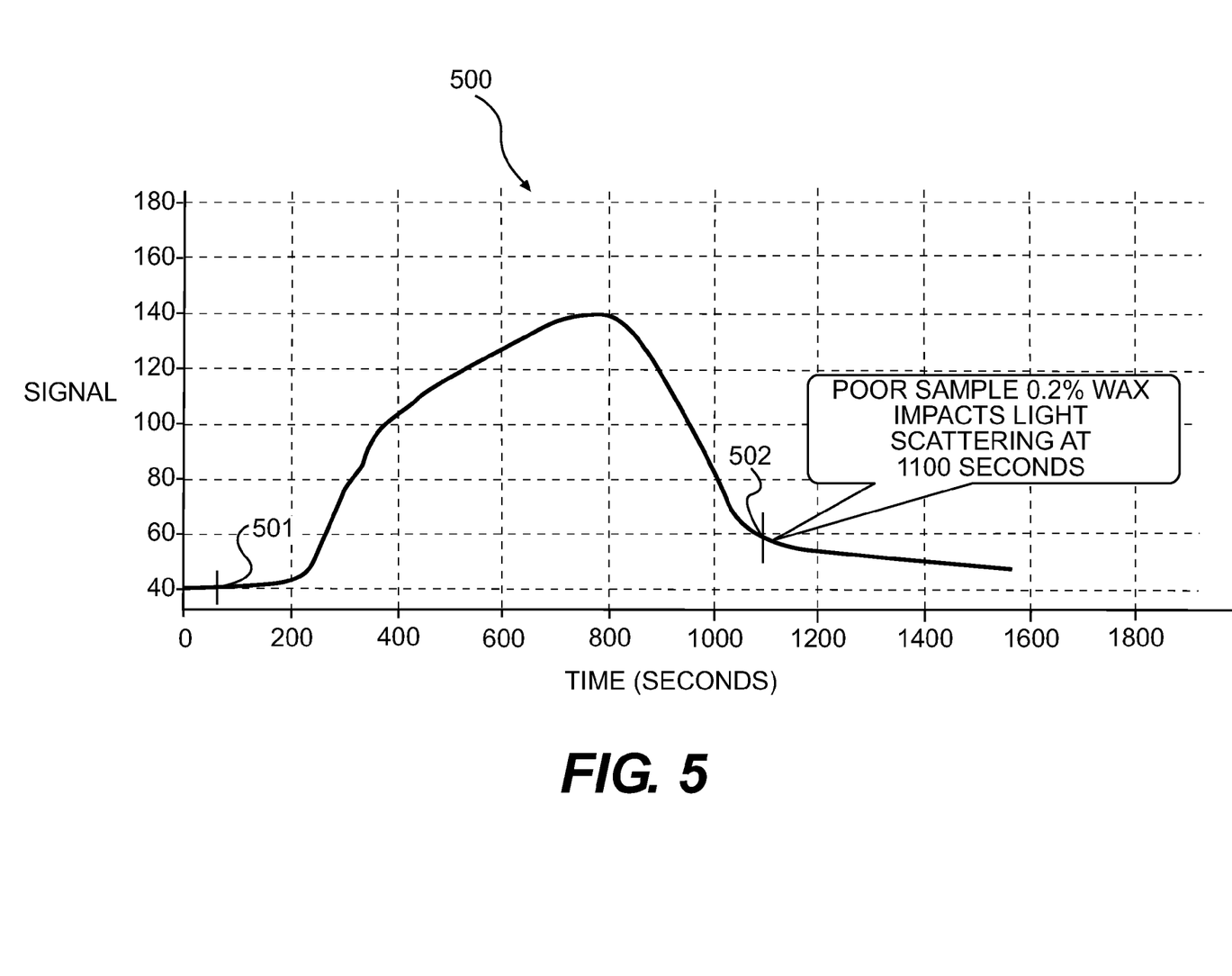
FIG. 5 is a plot 500 showing how the plot 300 in FIG. 3 changes when the sample of AC 600N in FIG. 3 is doped with 0.2% by weight wax and is no longer acceptable.

FIG. 5 shows the light scattering signal strength versus time curve 500 for the sample doped with 0.2% by weight wax. The signal strength at point 502, which is approximately 1100 seconds into the process during the 0° C. hold period, is noticeably higher than in FIG. 3 or 4 and, more importantly, noticeably higher than the baseline measurement 501 taken at the outset of the process and still changing. This test sample would not pass. The higher signal and noticeably steeper curve slope during the period the test sample is being held at 0° C. means that the HDT of the test sample is above 0° C. and the base stock represented by the test sample is likely to form long term haze.

Figure 6:
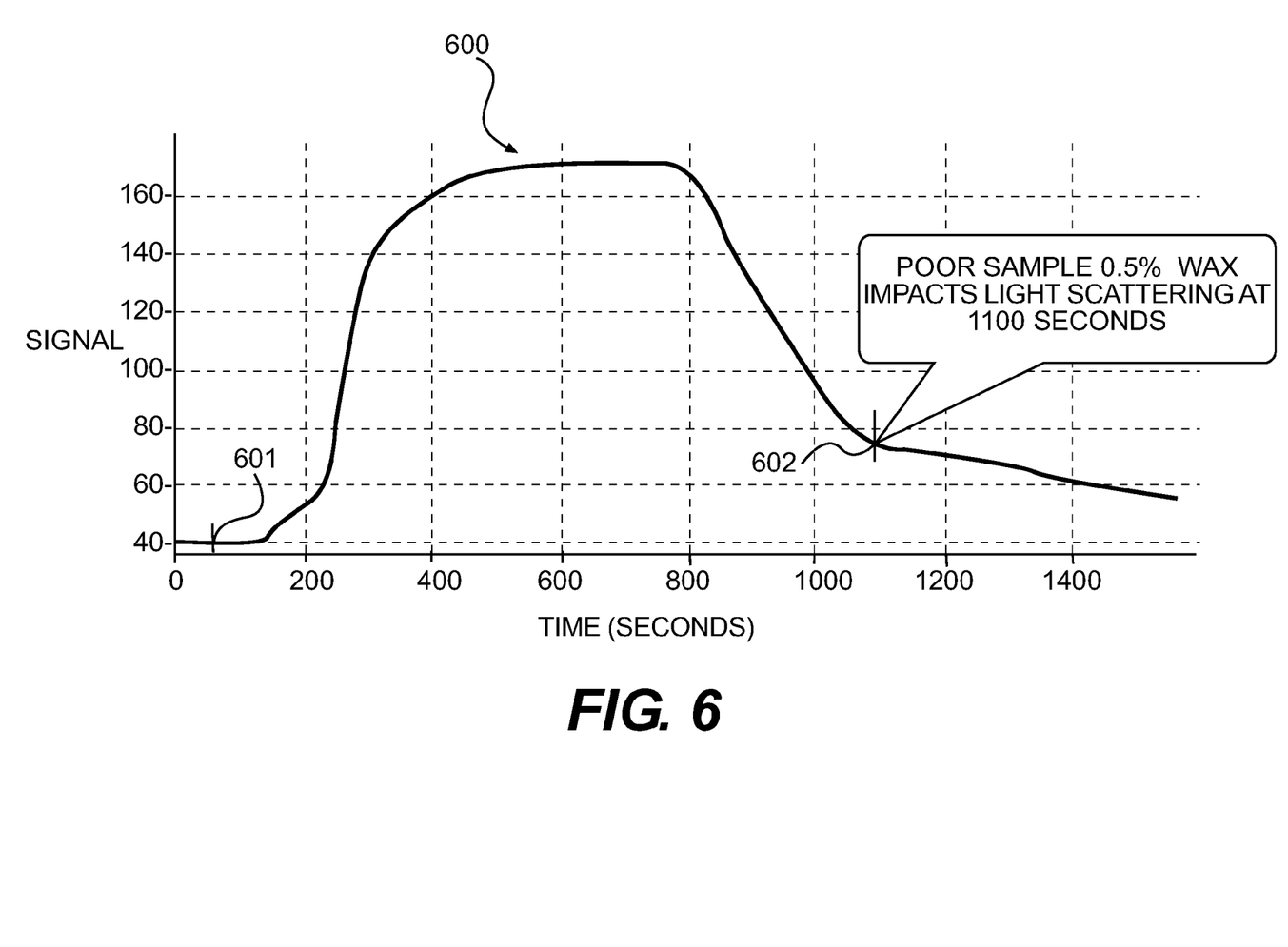
FIG. 6 is a plot 600 showing how the plot 300 in FIG. 3 changes when the sample of AC 600N in FIG. 3 is doped with 0.5% by weight wax and is no longer acceptable.

FIG. 6 shows the light scattering signal strength versus time curve 600 for the sample doped with 0.5% by weight wax. The signal strength at point 602, which is approximately 1100 seconds into the process during the 0° C. hold period, is noticeably higher than in FIG. 3, 4 or 5 and, more importantly, noticeably higher than the baseline measurement 601 taken at the outset of the process and still changing. This test sample would not pass. The higher signal and noticeably steeper curve slope during the period the test sample is being held at 0° C. means that the HDT of the test sample is above 0° C. and the base stock represented by the test sample is likely to form long term haze.

b. Example 2

Figure 7A:
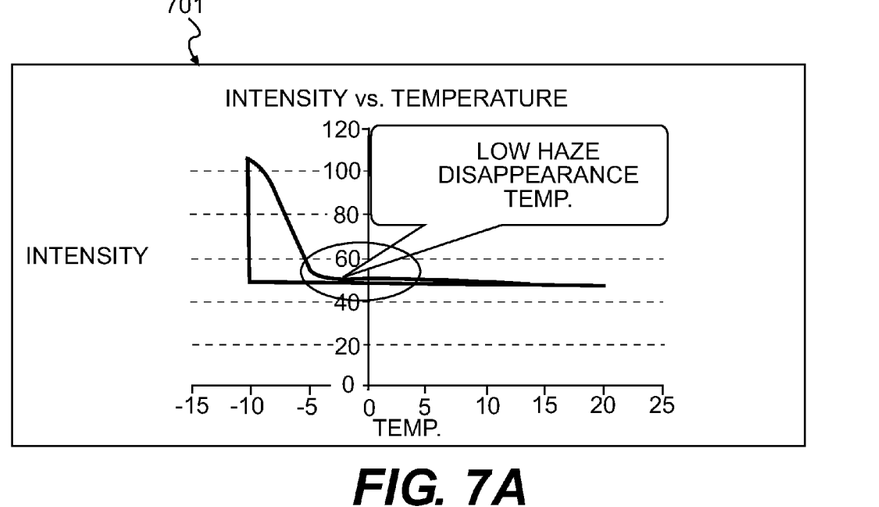
FIGS. 7A and 7B are a side by side comparison of a signal intensity versus time plot 701 and a signal intensity versus temperature plot 702, for a sample of AC 600N that was deemed acceptable using the technique of the invention.
Figure 7B:
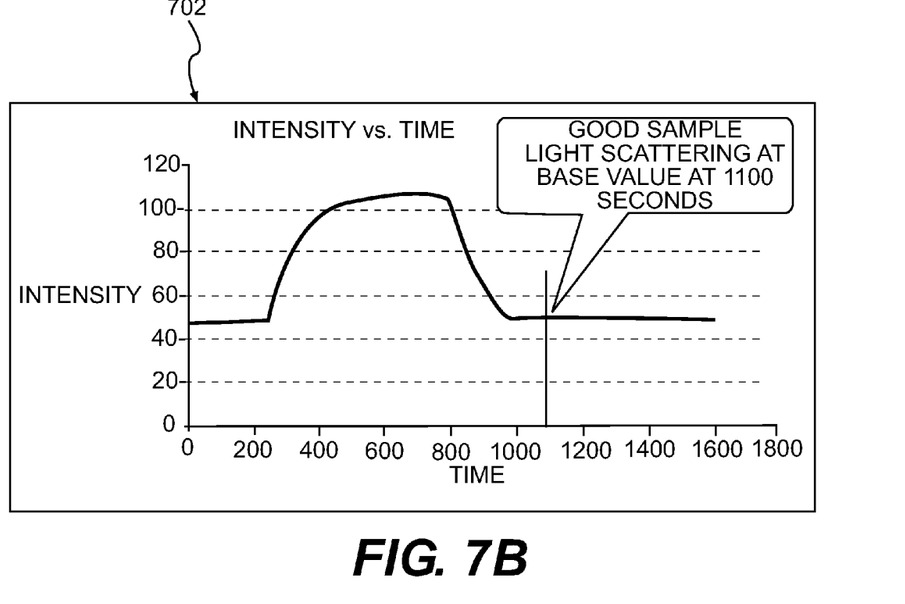
Figure 7C:
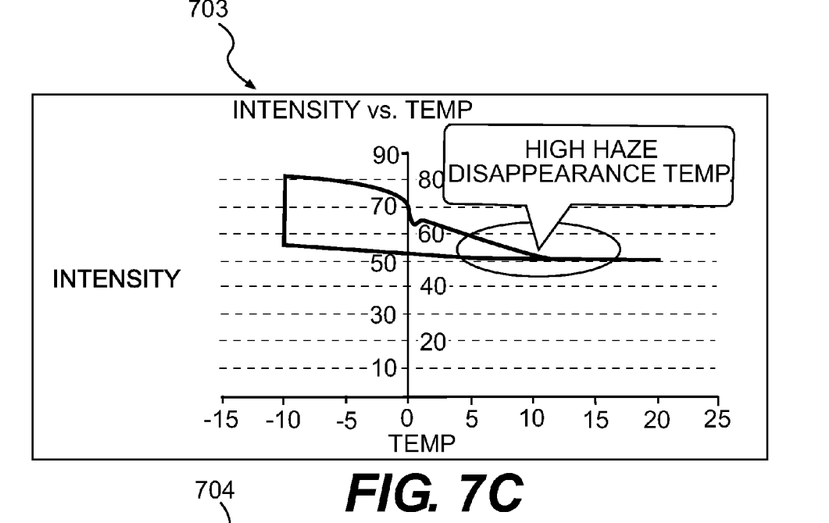
FIGS. 7C and 7D is a side by side comparison of a signal intensity versus time plot 703 and a signal intensity versus temperature plot 704 for a sample of another Heavy Neutral base stock called MCT 30 that was deemed unacceptable using the technique of the invention.
Figure 7D:
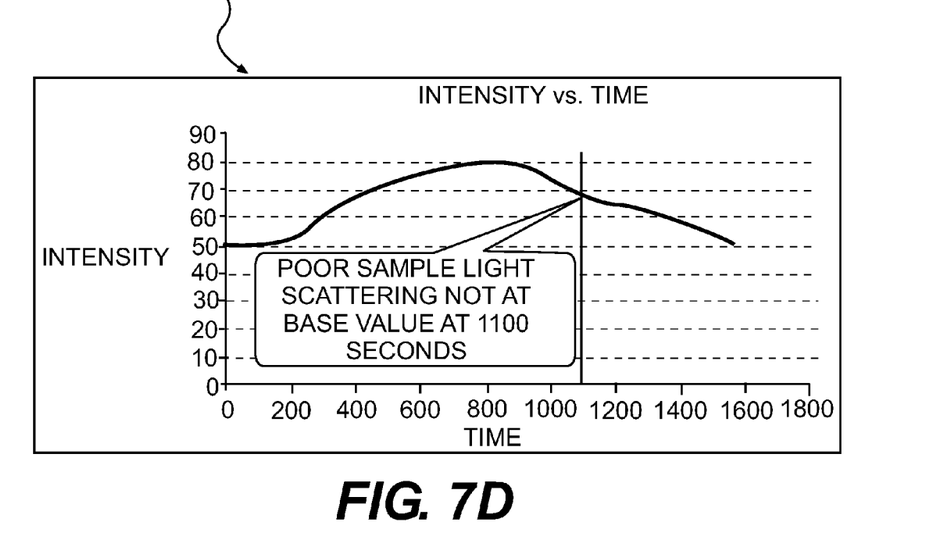

An alternate way of showing the behavior of the samples in the cooling and warm up cycle is through signal intensity vs. temperature plots. FIGS. 7A and 7B illustrate a comparison of a signal intensity vs. time plot 701 with signal intensity vs. temperature plot 702 for a good sample. FIGS. 7C and 7D illustrate a comparison of a signal intensity vs. time plot 703 with signal intensity vs. temperature plot 704 for a poor sample. As shown therein, for a good sample, the low HDT in FIG. 7A corresponds to light scattering near the base value at 1100 seconds in FIG. 7B. In contrast, for a bad sample, the high HDT in FIG. 7C corresponds to light scattering which is not near the base value at 1100 seconds in FIG. 7D.

c. Example 3

An approach similar to that taken for Heavy Neutrals was adopted for Bright base stock. Experiments were done with 1 part by eight oil: 3.2 parts by weight solvent mix (i.e., a 50:50 weight ratio MEK:MIBK mixture) and with a cool/soak to −10° C. A sudden drop in light scattering intensity during the soak period is observed and may be related to the structure of Bright base stock wax crystals which are precipitating and settling out. From several experiments done, it seems that the 600N test sample composition (1:3.2 dilution weight ratio and solvent composition of 50:50 weight ratio MEK:MIBK) is not as suitable for some Bright base stock samples.

Accordingly, a lower dilution weight ratio of oil:solvent (from 1:1 to 1:3.0 by weight) with different solvent compositions (e.g., MIBK mixed with 0%-50% by weight MEK) was evaluated to arrive at a better solvent composition and dilution ratio. A dilution ratio of around 1:2.0 oil:solvent by weight and a solvent composition (30:70 MEK:MIBK weight ratiot mixture) appears to be more effective for discriminating between a good and a poor Bright base stock samples.

Several Bright base stock samples were then evaluated using a 1:2 dilution ratio with a solvent composition (30 MEK:70MIBK) and a cool/soak at −10° C. Some samples with inherent low levels of wax did not show a good light scatter as the sample is cooled to −10° C. The samples were then put through a test that cools and soaks the sample to −15° C. A comparison of cool/soak at −10° C. vs −15° C. shows much improved light scatter when sample is cooled to −15° C. Accordingly, the optimum cool/soak temperature for Bright base stock appears to be −15° C. This is different than the cooling step in the temperature profile used for Heavy Neutral, which stopped at −10° C.

Refinery labs would prefer to have a single temperature profile for both 600N and Bright base stock for simplicity reasons. It was therefore decided to check if a cool/soak to −15° C. is also able to adequately differentiate between a good and a poor Heavy Neutral (600N). Runs were conducted on 600N with known lower levels of inherent wax and which did not give a good light scatter at −10° C. 600N runs at −15° C. have a much better light scatter and hence able to better differentiate samples with low levels of inherent wax compared to runs at −10° C.

Accordingly, the final recommended sample preparation step and cool/soak temperature for Heavy Neutrals and Bright base stock is as follows:

| Heavy Neutrals | Bright |
| --- | --- |
| 1 part oil sample + 3.2 parts of solvent mix by weight<br>Solvent composition: 50 MEK: 50 MIBK<br>Cool/soak to −15° C. | 1 part oil sample + 2 parts of solvent mix by weight<br>Solvent composition: 30 MEK: 70 MIBK<br>Cool/soak to −15° C. |

4.11 Incorporation by Reference

All publications, patents and patent applications mentioned in this specification are herein incorporated by reference to the same extent as if each individual publication, patent or patent application was specifically and individually indicated to be incorporated by reference. No admission is made that any reference cited herein is prior art.

4.12 Invention is Broader than the Specific Embodiments

The present invention is not to be limited in scope by the specific embodiments described herein. Various modifications of the present invention, in addition to those described herein, will be apparent to those of ordinary skill in the art from the foregoing description and accompanying drawings. Further, although the present invention has been described herein in the context of a particular implementation in a particular environment for a particular purpose, those of ordinary skill in the art will recognize that its usefulness is not limited thereto and that the present invention can be beneficially implemented in any number of environments for any number of purposes. Accordingly, the claims set forth below should be construed in view of the full breath and spirit of the present invention as disclosed herein.

What is claimed is:

1. A method for predicting future haze formation in dewaxed petroleum-derived lubricant base stocks, and products made there from, comprising the following steps: (1) preparing a test sample comprising a sample of neat base stock diluted with a solvent that facilitates the crystallization of wax components in the base stock, (2) subjecting the test sample to a temperature profile comprising a sub-ambient cooling and a subsequent heating step, (3) monitoring the crystallization and melting of wax in the test sample, including but not limited to the HDT, during the course of the temperature ramp, by measuring, directly or indirectly, changes in light scattering; and (4) using a comparison of the HDT determined by light scattering to a HDT reference point determined from historical test data to determine whether the base stock exhibits an acceptable or unacceptable potential for forming haze over the course of a lubricant manufacture, storage and use lifecycle.

2. A method for predicting future haze formation in a dewaxed, petroleum based, lubricant base stock, and products made there from, comprising the followings steps:
(i) diluting a sample of the neat base stock in a solvent that facilitates crystallization of wax components;
(ii) subjecting the test sample to a temperature ramp that at least comprises—
  (a) a cooling step whereby the test sample is cooled to a sub-ambient target temperature and held there for a period of time sufficient to crystallize high melting wax components in the base stock, and
  (b) a subsequent heating step whereby the test sample is heated to a target temperature sufficiently high, and at a rate that is sufficiently slow, to accurately measure the temperature at which the crystallized wax has fully melted back into solution (i.e., the haze disappearance temperature (HDT));
(iii) monitoring the crystallization and melting of wax in the test sample, including but not limited to the HDT, during the course of the temperature ramp, by measuring, directly or indirectly, changes in light scattering; and
(iv) using a comparison of the HDT determined by light scattering to a HDT reference point determined from historical test data to determine whether the base stock exhibits an acceptable or unacceptable potential for forming haze over the course of a lubricant manufacture, storage and use lifecycle.

3. The method of claim 2 where the base stock is a Neutral or Bright base stock manufactured to meet group I, group II or group III specifications.

4. The method of claim 2 where the base stock is a Heavy Neutral or Bright base stock manufactured to meet group I specifications.

5. The method of claim 2, where the solvent has a bulk solubility parameter that lies at least 0.1 $MPa^{1/2}$ above the solubility parameter of the base oil being tested and wax.

6. The method of claim 5, where the solvent is a blend of two or more solvent components having a solubility parameter differential no greater than 5 $MPa^{1/2}$.

7. The method of claim 6, where the solvent is a blend of two or more solvent components selected from the group consisting of ketones, toluene, ethers and acetone.

8. The method of claim 7, where the solvent is a blend of methyl iso-butyl ketone (MIBK) and methyl ethyl ketone, (MEK).

9. The method of claim 5 where the base oil has a solubility parameter that is anywhere from 0.2-2.0 $MPa^{1/2}$ above the solubility parameter of the base oil.

10. The method of claim 2 where the weight ratio of base stock to solvent is 1:1-5.

11. The method of claim 2, where the weight ratio of base stock to solvent is 1:1-3.5.

12. The method of claim 2, where the temperature ramp additionally comprises a first pre-heating step, prior to the aforementioned cooling and heating steps, where the test sample is first heated for a time and to a temperature sufficient to melt any crystallized wax present in the test sample at ambient temperature.

13. The method of claim 2, where the test sample is cooled to a target temperature below ambient temperature, and held at the target temperature for a period of time, sufficient to crystallize a majority of high melting wax components in the base stock.

14. The method of claim 2 where the test sample is cooled to, and held at, a target temperature that is below 0° C. and above the base stock's cloud point for a period ranging from 5 to 60 minutes.

15. The method of claim 2 where the test sample, after the cooling step, is heated at a rate ranging from 0.1 to 1° C. per minute to temperature that is at least above 0° C.

16. The method of claim 2 where changes in scattering of light in the ultraviolet, visible and/or infrared portion of the spectrum are monitored directly or indirectly over the course of the temperature profile.

17. The method of claim 2 where the steps are performed in two hours or less.

18. A real time method for predicting future haze formation in a group I base stock selected from Heavy Neutrals and Bright base stock, at least comprising the followings four steps:
(i) diluting a sample of the base stock in a solvent comprising a 10:90 to 90:10 blend of methyl ethyl ketone and methyl isobutyl ketone at a base stock to solvent ratio of 1:1-5;
(ii) subjecting the test sample to a temperature ramp that at least comprises at least the following steps in the following order—
  (a) a pre-heating step, where the test sample is first heated for a time and to a temperature sufficient to melt crystallized wax already present in the test sample in order to obtain a light scattering measurement to serve as a baseline;
  (b) a cooling step whereby the test sample is cooled to, and held at, a target temperature that is below 0° C. and above the base stock's cloud point, for a period ranging from 5 to 60 minutes, in order to crystallize high melting wax components in the base stock, and
  (c) a second heating step whereby the test sample heated at a rate ranging from 0.1 to 1° C. per minute to temperature that is at least above 0° C., in order to measure temperature at which the crystallized wax has fully melted back into solution (i.e., the haze disappearance temperature);
(iii) monitoring the crystallization and melting of wax, during the course of the cooling and heating temperature ramp, by measuring changes in light scattering that correspond to the formation and melting of wax crystals in the test sample; and
(iv) utilizing a haze disappearance temperature as an indicator of long term haze potential, wherein a haze disappearance temperature greater than 0° C. is an indicator that the base stock has an unacceptable risk of forming long term haze.

19. The method of claim 18 where the base stock is a Heavy Neutral, where the methyl ethyl ketone to methyl isobutyl ketone weight ratio ranges from 20-80:80-20 and the weight ratio of base stock to solvent ranges from 1:2-4.

20. The method of claim 18 where the base stock is a Heavy Neutral, where the methyl ethyl ketone to methyl isobutyl ketone weight ratio is approximately 50:50 and the weight ratio of base stock to solvent is approximately 1:3.2.

21. The method of claim 18 where the base stock is a Bright base stock, where the weight ratio of methyl ethyl ketone to methyl isobutyl ketone ranges from 20-40 to 80:60 and where the weight ratio of base stock to solvent ranges from 1:1-3.

22. The method of claim 18 where the base stock is a Bright base stock, where the weight ratio of methyl ethyl ketone to methyl isobutyl ketone is approximately 30:70 and where the weight ratio of base stock to solvent is approximately 1:2.

* * * * *